United States Patent [19]
Yoshida et al.

[11] Patent Number: 6,006,586
[45] Date of Patent: Dec. 28, 1999

[54] METHOD OF MEASURING GAS CONCENTRATION

[75] Inventors: Toshihiro Yoshida; Naoyuki Ogawa, both of Nagoya; Tomonori Takahashi, Chita, all of Japan

[73] Assignee: NGK Insulators, Ltd., Japan

[21] Appl. No.: 09/036,068

[22] Filed: Mar. 6, 1998

[30] Foreign Application Priority Data

Mar. 19, 1997 [JP] Japan .................................. 9-066020

[51] Int. Cl.⁶ ...................................................... G01N 7/12
[52] U.S. Cl. .......................... 73/31.06; 73/23.2; 73/31.04
[58] Field of Search .................................. 73/23.2, 31.05, 73/31.06, 31.04

[56] References Cited

U.S. PATENT DOCUMENTS

| 5,602,326 | 2/1997 | Takahashi et al. | 73/31.06 |
| 5,705,129 | 1/1998 | Takahashi et al. | 73/23.31 X |
| 5,763,763 | 6/1998 | Kato et al. | 73/23.2 |

FOREIGN PATENT DOCUMENTS

| 0 737 859 A1 | 10/1996 | European Pat. Off. . |
| 3804486 A1 | 8/1989 | Germany . |
| 61-147145 | 7/1986 | Japan | 73/31.05 |
| 6-222028 | 8/1994 | Japan . |
| 7-20075 | 1/1995 | Japan . |
| WO 85 01351 | 3/1985 | WIPO . |

OTHER PUBLICATIONS

Patent Abstracts of Japan vol. 098, No. 002, Jan. 30, 1998 & JP 09264861 A (NGK Insultars Ltd), Oct. 7, 1997.

*Primary Examiner*—Daniel S. Larkin
*Attorney, Agent, or Firm*—Wall Marjama Bilinski & Burr

[57] ABSTRACT

A method of measuring a gas concentration for measuring any one of the concentrations of NOx, $NO_2$, NO, and $O_2$ by using one or more sensor elements utilizing a metal oxide semiconductor as a sensing element is disclosed. In the method of measuring a gas concentration, any one of the partial pressures of $NO_2$, NO, and $O_2$ is calculated on the basis of the following formula (1), and any one of the concentrations of NOx, $NO_2$, NO, and $O_2$ is measured on the basis of the calculated partial pressure;

$$\frac{1}{R} = Q - \frac{AP_{NO2} + BP_{NO} + CP_{O2}^{1/2} + DP_{NO}P_{O2}^{1/2}}{1 + EP_{NO2} + FP_{NO} + GP_{O2}^{1/2} + HP_{NO}P_{O2}^{1/2}} \quad (1)$$

wherein R is resistance and A–H and Q are constant.

7 Claims, 2 Drawing Sheets

1

METHOD OF MEASURING GAS CONCENTRATION

BACKGROUND OF THE INVENTION

1. Field of the Invention

The present invention relates to a method of measuring a gas concentration for measuring any one of concentrations of NOx, $NO_2$, NO, and $O_2$ by using a sensor element utilizing a metal oxide semiconductor as a sensing element.

2. Prior Art Statements

Usually, as a method of measuring NOx concentration in a gas to be measured including NOx, such as a combustion exhaust gas from an incinerator, a method for sampling a gas to be measured including NOx concentration in for example a gas duct, and measuring NOx concentration in the thus sampled gas by using an optical measuring apparatus is known. However, the optical measuring apparatus mentioned above is very expensive. Moreover, since it needs a gas sampling, there is a drawback such that a responsibility becomes worse.

In order to solve the drawback mentioned above, a semiconductor sensor of a gas duct direct insertion type has been used, recently. For example, Japanese Patent Laid-Open Publication No. 6-222028 (JP-A-6-222028) discloses a NOx sensor comprising a sensing portion made of a predetermined oxide of perovskite type, and a conduction measuring portion for measuring a conductivity of the sensing portion.

However, even in the semiconductor sensor of a gas duct direct insertion type mentioned above, any countermeasure for an influence of $O_2$ and CO included in a gas to be measured with respect to a NOx measurement value is not taken. Moreover, a resistance of the sensing portion is normally varied corresponding to an amount of NOx($NO_2$+ NO)) i.e. a concentration thereof. However, in the case that an amount (concentration) ratio between $NO_2$ and NO is varied, i.e. in case that a partial pressure ratio between $NO_2$ and NO is varied, a resistance measured by the sensing portion is varied even if an amount of NOx is constant. Therefore, the semiconductor sensor mentioned above can not sense only NOx selectively. Accordingly, the semiconductor sensor of a gas duct direct insertion type mentioned above has a drawback,such that a NOx concentration in a gas to be measured can not be measured in a highly precise and selective manner, even if it is inexpensive and has an excellent responsibility as compared with the optical measuring apparatus.

On the other hand, in Japanese Patent Laid-Open Publication No. 7-20075 (JP-A-7-20075), there is disclosed a method of measuring a gas concentration in which concentrations of respective gas components are measured by using a predetermined formula utilizing detectors the number of which is equal to that of gas components to be measured. However, if the method mentioned above is applied to a NOx measurement, it is not possible to completely eliminate an influence of $O_2$ with respect to a NOx measurement value, since this method uses a linear formula.

SUMMARY OF THE INVENTION

An object of the invention is to eliminate the drawbacks mentioned above and to provide a method of measuring a gas concentration in which any one of concentrations of NOx, $NO_2$, NO, and $O_2$ can be measured in a highly precise and selective manner.

According to the invention, a method of measuring a gas concentration for measuring any one of concentrations of NOx, $NO_2$, NO and $O_2$ by using one or more sensor elements utilizing a metal oxide semiconductor as a sensing element, comprising the steps of: calculating any one of partial pressures of $NO_2$, NO, and $O_2$ on the basis of the following formula (1);

$$\frac{1}{R} = Q - \frac{AP_{NO2} + BP_{NO} + CP_{O2}^{1/2} + DP_{NO}P_{O2}^{1/2}}{1 + EP_{NO2} + FP_{NO} + GP_{O2}^{1/2} + HP_{NO}P_{O2}^{1/2}} \quad (1)$$

wherein R is resistance and A–H and Q are constant; and measuring any one of the concentrations of NOx, $NO_2$, NO and $O_2$ on the basis of the calculated partial pressure.

In the present invention, the formula (1) mentioned above showing a relation between partial pressures $P_{NO2}$, $PN_O$, and $P_{O2}$ of $NO_2$, NO, and $O_2$ and a resistance R in the sensor element utilizing metal oxide semiconductor as a sensing element is preliminarily obtained. Then, in an actual measurement, if all the three partial pressures are unknown, three sets of the formula (1) are prepared by using three sensor elements. If one of three partial pressures is known and the other two partial pressures are unknown, two sets of the formula (1) are prepared by using two sensor elements. If two of three partial pressures are known and the other one partial pressure is unknown, one set of the formula (1) is prepared by using one sensor element. In this case, if a total pressure of a gas to be measured is known, respective partial pressures of $NO_2$, NO, and $O_2$ correspond directly to respective gas concentrations. Therefore, it is possible to measure concentrations of $NO_2$, NO, and $O_2$ from the measured partial pressures of $NO_2$, NO, and $O_2$. Moreover, a concentration of NOx can be measured from a total concentrations of $NO_2$ and NO.

DESCRIPTION OF THE PREFERRED EMBODIMENTS

Figure 1:
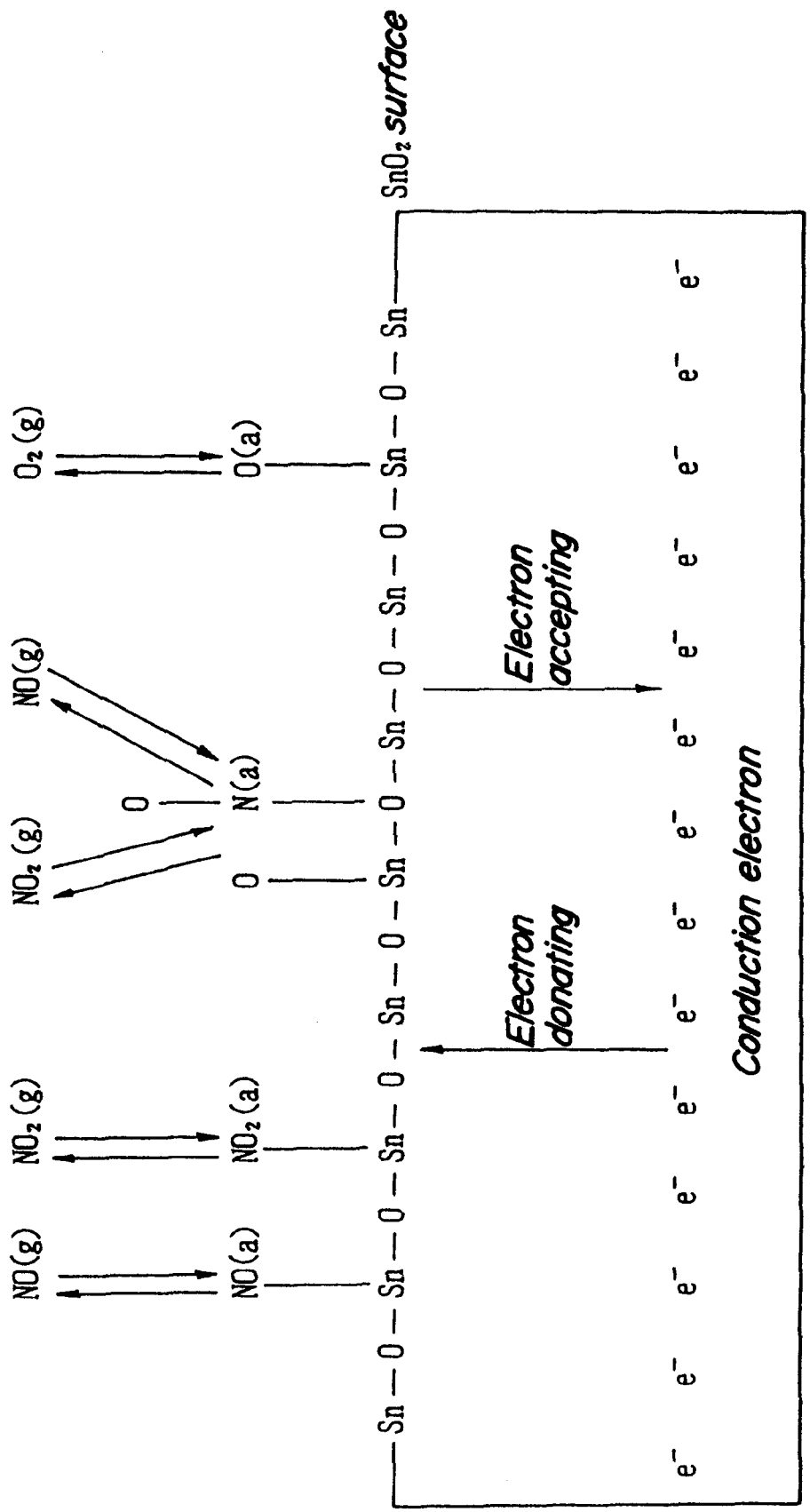
FIG. 1 is a schematic view showing a mechanism of a method of measuring a gas concentration according to the present invention.

At first, a reaction mechanism in a method of measuring a gas concentration according to the invention will be explained. FIG. 1 is a schematic view in which a gas adsorption behavior on an $SnO_2$ surface at 550° C. is modeled. The present inventors confirm from a result of FT-IR (Fourier Transform Infrared Sn—$O_2$NO on the $SnO_2$ surface under an atmosphere including NO and $NO_2$. Moreover, since it is known that $O_2$ is dissociatively adsorbed on a metal in oxide at a temperature higher than 500° C., and since it is known that an adsorption peak disappears if $O_2$ is introduced into $NO/N_2$ atmosphere, it is understood that $O_2$ is adsorbed in a form of Sn—O and is competitively adsorbed with respect to NO and $NO_2$ whose common adsorption site is Sn. Moreover, both of NO and $NO_2$ have a common adsorbate of Sn—$O_2$ NO, and thus it is understood that this common adsorbate means a reaction intermediate member of NO oxidizing reaction: $2NO+O_2 = 2NO_2$. Further, it is understood from a result of TPD (Temperature Programmed Desorption) that these adsorbates are in an equilibrium state at 550° C. On the basis of the results mentioned above, a model of gas adsorption behavior on the $SnO_2$ surface at 550° C. can be obtained as shown in FIG. 1. That is to say, the following formula (1) can be obtained on the basis of the model in which the adsorbates are competitively adsorbed, as shown in FIG. 1 and a conduction electron is removed from $SnO_2$;

$$\frac{1}{R} = Q - \frac{AP_{NO2} + BP_{NO} + CP_{O2}^{1/2} + DP_{NO}P_{O2}^{1/2}}{1 + EP_{NO2} + FP_{NO} + GP_{O2}^{1/2} + HP_{NO}P_{O2}^{1/2}} \quad (1)$$

wherein R is resistance and A–H and Q are constant. In FIG. 1, (g) shows a gaseous state and (a) illustrates an adsorption state.

Figure 2:
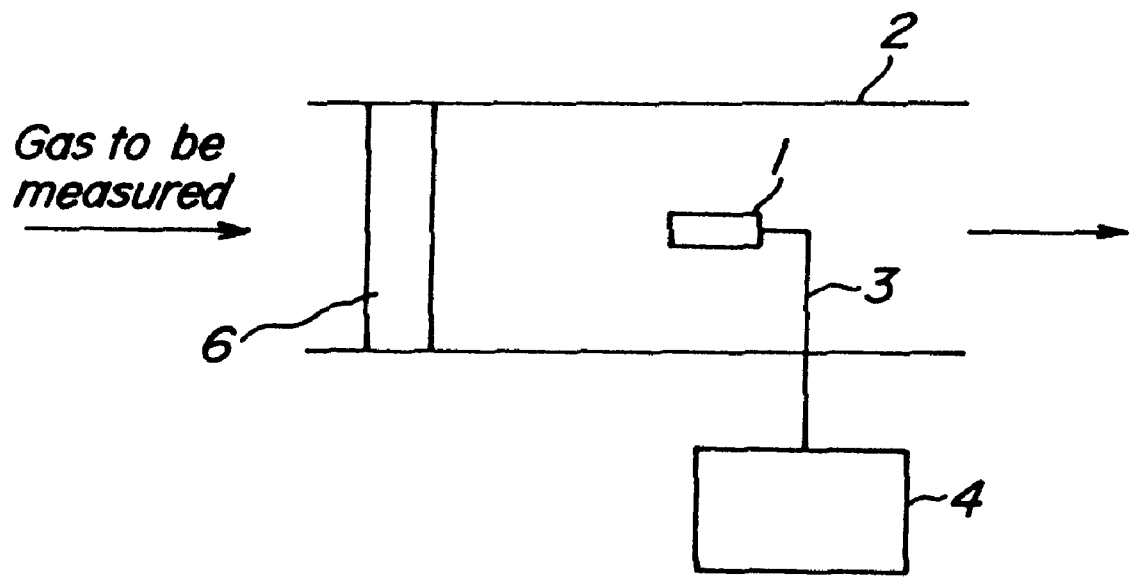
FIG. 2 is a schematic view illustrating one embodiment of an apparatus which performs a method of measuring a gas concentration according to the present invention.

FIG. 2 is a schematic view showing one embodiment of an apparatus which performs a method of measuring a gas concentration according to the invention. In the embodiment mentioned above, numeral 1 is a sensor element in which a metal oxide semiconductor member inserted into a gas duct 2 is used as a sensing element, numeral 3 is a cable, and numeral 4 is a processing portion in which a resistance measured by the sensor element 1 is received and a predetermined calculation based on the formula (1) mentioned above is performed with respect to the thus received resistance to obtain one of concentrations of $NO_2$, NO, and $O_2$. As the metal oxide semiconductor, one of $In_2O_3$, $SnO_2$) and NiO is preferably used.

The embodiment mentioned above shows an embodiment using only one sensor element 1 in which, among partial pressures of $NO_2$, NO, and $O_2$ to be measured, two of them are known and the other one is unknown. Moreover, numeral 6 is a catalyst, preferably,made of Pt for making a partial pressure ratio of $NO/NO_2$ in an equilibrium state and for removing CO, which is previously proposed by the applicant. In this embodiment, if the apparatus is constructed in such a manner that a gas to be measured which passes through the catalyst is brought into contact with the sensor element 1, a relation between the resistance measured by the sensor element 1 and a concentration of NO can be determined one by one, and thus it is possible to perform a highly precise measurement.

Hereinafter, actual examples will be explained.

Example According to the Invention

In order to confirm an effectivity of the formula (1) mentioned above for a method of measuring a gas concentration according to the invention, a test was performed by preparing a sensor element having a sensing element made of $SnO_2$, obtaining constants in the formula (1) by performing a calibration for the sensor element, introducing $NO_2$, NO and $O_2$ gasses each having a known partial pressure actually to the sensor element, and comparing the known partial pressure and a partial pressure calculated from the formula (1) on the basis of a resistance measured by the sensor element at that time. The followings are detailed explanations.

(1) Element Manufacturing:

At first, tin oxide was hydrolyzed by aqueous ammonia, and the hydrolyzed tin oxide was subjected to a filtration and separation. After that, the filtered tin oxide was subjected to a thermal decomposition at 600° C. for two hours to obtain tin oxide powders. The thus obtained tin oxide powders were mixed in a wet state for ten hours in a mixture solvent of acetone and 2-ethylhexanol with organic binders and plasticizers by using zirconia media. After that, acetone was vaporized to obtain an element printing ink. As a substrate of a sensor element, an alumina plate having a dimension of 1×5×65 mm was used. Platinum electrodes and platinum heaters were preliminarily printed on the substrate, and the thus obtained element printing ink was printed at a tip portion of the electrodes. Then, the substrate was sintered at 800° C. for two hours to obtain the sensor element. In the case that the sensor element includes Ta, tantalum oxide was added with organic binders in the mixture solvent during the wet mixture step. In this embodiment, an amount of Ta was 3 wt % with respect to the Sn atom.

(2) Calibration:

As shown in the following Table 1, nine kinds of test gases each having predetermined and arbitrary partial pressures of $NO_2$, NO, and $O_2$ were prepared. The thus prepared test gas was introduced into an apparatus having the same construction shown in FIG. 2, but arranging no catalyst 6 at an upstream position of the sensor element 1. At that time, a resistance of the sensor element 1 was measured. This measurement was performed for all nine test gasses to obtain nine resistances. Then, constants A–H and Q in the formula (1) were calculated by using the nine resistances. The results of the calculated constants are shown the following Table 2.

TABLE 1

|   | $P_{NO2}$ (atm) | $P_{NO}$ (atm) | $P_{O2}$ (atm) | R (Ω) |
|---|---|---|---|---|
| 1 | 1.21E − 05 | 8.78E − 06 | 1.00E − 05 | 389440 |
| 2 | 6.67E − 06 | 4.03E − 06 | 1.00E − 03 | 399875 |
| 3 | 1.33E − 05 | 7.56E − 06 | 2.00E − 01 | 497843 |
| 4 | 2.80E − 05 | 2.44E − 05 | 1.00E − 02 | 382278 |
| 5 | 3.13E − 05 | 2.11E − 05 | 2.00E − 01 | 486698 |
| 6 | 0.00E + 00 | 0.00E + 00 | 1.00E − 01 | 90032 |
| 7 | 6.32E − 06 | 4.38E − 06 | 1.00E − 01 | 411402 |
| 8 | 0.00E + 00 | 0.00E + 00 | 1.00E − 03 | 18415 |
| 9 | 3.27E − 06 | 2.03E − 06 | 1.00E − 02 | 354808 |

TABLE 2

| Q | 1.05E − 04 |
|---|---|
| A | 4.29E + 03 |
| B | 3.18E + 02 |
| C | 3.12E − 03 |
| D | 1.30E + 02 |
| E | 4.14E + 07 |
| F | 3.83E + 06 |
| G | 3.01E + 01 |
| H | 8.32E + 05 |

(3) Comparison Measurement:

A mixed gas in which partial pressures of $NO_2$ and NO were known and a partial pressure of $O_2$ was 0.2 atm was prepared, and the thus prepared mixed gas was introduced into an apparatus having the same construction shown in FIG. 2 to measure a resisstance of the sensor element 1. In this case, a temperature of the sensor element 1 was maintained at 550° C. Moreover, a temperature of the catalyst 6 was maintained at 400° C. Further, a ratio of NO/NOx was maintained at 0.35. Then, by using the formula (1) mentioned above showing a relation between the thus measured resistance and a partial pressure and also using relations of $P_{NOx}=P_{NO}+P_{NO2}$ and $P_{NO}/P_{NOx}=0.35$, a partial pressure of NOx was calculated. Then, the thus calculated partial pressure of NOx was compared with a predetermined partial pressure of NOx by using a deviation defined as deviation (%)=|calculated NOx−predetermined NOx|/predetermined NOx. The results are shown in the following Table 3.

TABLE 3

| Resistance R ($\Omega$) | Calculated $NO_x$ | Predetermined $NO_x$ | Deviation (%) |
|---|---|---|---|
| 534800 | 5.84E − 05 | 5.87E − 05 | 0.56 |
| 512300 | 2.37E − 05 | 2.33E − 05 | 1.70 |
| 472300 | 1.06E − 05 | 1.07E − 05 | 1.24 |
| 452700 | 8.01E − 06 | 7.99E − 06 | 0.22 |
| 412900 | 5.03E − 06 | 5E − 06 | 0.62 |
| 369200 | 3.26E − 06 | 3.22E − 06 | 1.17 |

From the results shown in Table 3, since the thus measured deviations are little, a partial pressure of the calculated NOx obtained on the basis of the formula (1) according to the invention is substantially the same as that of the predetermined NOx. Therefore, an effectivity of a method of measuring a gas concentration by using the formula (1) can be confirmed.

Comparative Example

As a comparative example, an example in which a relation between a partial pressure and a resistance was assumed to be linear, was investigated by using the same sensor element and catalyst as those of the example according to the invention and by using an apparatus having the same construction shown in FIG. 2. In this case, a formula to be used was $R = lP_{NO2} + mP_{NO} + nP_{O2}$. At first, as is the same as the example according to the invention, the same calibration was performed to obtain constants l, m, and n in the above formula, and then the comparison measurement was performed. The followings are detailed explanations.

(1) Element Manufacturing:

A sensor element according to the comparative example was manufactured in the same manner as that of the example according to the invention.

(2) Calibration:

As shown in the following Table 4, three kinds of test gases each having predetermined and arbitrary partial pressures of $NO_2$, NO, and $O_2$ were prepared. The thus prepared test gas was introduced into an apparatus having the same construction shown in FIG. 2, but arranging no catalyst 6 at an upstream position of the sensor element 1. At that time, a resistance of the sensor element 1 was measured. This measurement was performed for all the test gases to obtain three resistances. Then, constants l, m, and n in the above formula were calculated by using three resistances. The results of the calculated constants are shown in the following Table 5.

TABLE 4

| | $PN_{O2}$ (atm) | $P_{NO}$ (atm) | $P_{O2}$ (atm) | R ($\Omega$) |
|---|---|---|---|---|
| 1 | 1.21E − 05 | 8.78E − 06 | 1.00E − 05 | 389440 |
| 2 | 1.33E − 05 | 7.56E − 06 | 2.00E − 01 | 497843 |
| 3 | 0.00E + 00 | 0.00E + 00 | 1.00E − 03 | 18415 |

TABLE 5

| | |
|---|---|
| l | −1.21E + 12 |
| m | 1.72E + 12 |
| n | 1.84E + 7 |

(3) Comparison Measurement:

With respect to a gas having a predetermined partial pressure of NOx, as is the same as the example according to the invention, a resistance of the sensor element and a calculated partial pressure of NOx obtained on the basis of the above formula were measured, and the predetermined partial pressure of NOx and the calculated partial pressure of NOx were compared with each other by using a deviation. The results are shown in the following Table 6. From the results shown in Table 6, in the comparative example, since the calculated partial pressure of NOx is largely deviated from the predetermined partial pressure of NOx, it is confirmed that a measurement precision using a linear formula is worse.

TABLE 6

| Resistance R ($\Omega$) | Calculated $NO_x$ | Predetermined $NO_x$ | Deviation (%) |
|---|---|---|---|
| 534800 | 1.69E − 05 | 5.87E − 05 | 248.20 |
| 512300 | 1.70E − 05 | 2.33E − 05 | 37.23 |
| 472300 | 1.72E − 05 | 1.07E − 05 | 37.77 |
| 452700 | 1.73E − 05 | 7.99E − 06 | 53.81 |
| 412900 | 1.75E − 05 | 5E − 06 | 71.45 |
| 369200 | 1.77E − 05 | 3.22E − 06 | 81.85 |

In the embodiments mentioned above, one sensor element is used as shown in FIG. 2. However, according to the invention, in the case that all the partial pressures of three kinds of gases i.e. $NO_2$, NO, and $O_2$ are unknown, it is possible to perform a method of measuring a gas concentration according to the invention in such a manner that three sets of the above formula (1) are obtained by using a sensor element utilizing three different oxide semiconductors and the respective gas concentration are measured. In addition, it is possible to perform a method of measuring a gas concentration according to the invention by using a sensor element utilizing two different oxide semiconductors and one means of measuring $O_2$ partial pressure.

As clearly understood from the above explanations, according to the invention, partial pressures of $NO_2$, NO, and $O_2$ can be obtained by calculating three resistances of the sensor element on the basis of the above formula (1), and thus respective concentrations of $NO_2$, NO, and $O_2$ can be obtained from the thus obtained partial pressures, so that it is possible to measure one of concentrations of NOx, $NO_2$, NO, and $O_2$ in a highly precise manner.

What is claimed is:

1. A method of measuring a gas concentration for measuring any one of concentrations of NOx, $NO_2$, NO, and $O_2$ by using one or more sensor elements utilizing a metal oxide semiconductor as a sensing element, comprising the steps of:

calculating any one of the partial pressures of $NO_2$, NO, and $O_2$ on the basis of the following formula (1);

$$\frac{1}{R} = Q - \frac{AP_{NO2} + BP_{NO} + CP_{O2}^{1/2} + DP_{NO}P_{O2}^{1/2}}{1 + EP_{NO2} + FP_{NO} + GP_{O2}^{1/2} + HP_{NO}P_{O2}^{1/2}} \quad (1)$$

wherein R is resistance and A–H and Q are constants; and measuring any one of concentrations of NOx, $NO_2$, NO, and $O_2$ on the basis of the calculated partial pressure.

2. The method according to claim 1, wherein one of $In_2O_3$, $SnO_2$, and NiO is used as said metal oxide semiconductor.

3. The method according to claim 1, wherein a gas to be measured is passed through a catalyst for making a partial pressure ratio of $NO/NO_2$ in an equilibrium state and for removing a CO component in the gas to be measured prior to being contacted with the gas sensor.

4. The method according to claim 1, wherein the nine constants A–H and Q in the formula (1) are obtained prior to an actual measurement by performing a calibration in such a manner that (a) nine kinds of gases each having predetermined and arbitrary partial pressures of $NO_2$, NO, and $O_2$ are prepared, (b) the thus prepared gases are brought into contact with the sensor element successively to obtain nine resistances of the sensor element, and (c) the nine constants A–H and Q are calculated from nine sets of the formula (1).

5. The method according to claim 1, wherein, if all the three partial pressures of $NO_2$, NO, and $O_2$ in a gas to be measured are unknown, three sets of the formula (1) are prepared by using three sensor elements to obtain three unknown partial pressures.

6. The method according to claim 1, wherein, if one of three partial pressures of $NO_2$, NO, and $O_2$ in a gas to be measured is known and the other partial pressures are unknown, two sets of the formula (1) are prepared by using two sensor elements to obtain two unknown partial pressures.

7. The method according to claim 1, wherein, if two of three partial pressures of $NO_2$, NO, and $O_2$ in a gas to be measured are known and the other one partial pressure is unknown, one set of the formula (1) is prepared by using one sensor element to obtain one unknown partial pressure.

* * * * *